United States Patent [19]

Sisti et al.

[11] 4,271,695

[45] Jun. 9, 1981

[54] APPARATUS FOR FEEDING CARRIER GAS TO ON-COLUMN INJECTORS

[75] Inventors: Giorgio Sisti, Melzo, Italy; Sorin Trestianu, Iselles, Belgium; Mario Galli, Legnano, Italy

[73] Assignee: Carlo Erba Strumentazione S.p.A., Rodano, Italy

[21] Appl. No.: 82,252

[22] Filed: Oct. 5, 1979

[30] Foreign Application Priority Data

Oct. 16, 1978 [IT] Italy .................... 23060/78[U]

[51] Int. Cl.³ .......................................... G01N 31/08
[52] U.S. Cl. .................................................. 73/23.1
[58] Field of Search ................. 73/23.1; 55/67, 197, 55/386; 422/89

[56] References Cited

U.S. PATENT DOCUMENTS

| 3,240,052 | 3/1966 | Reinecke et al. | 73/23.1 |
| 4,196,612 | 4/1980 | Clardy et al. | 73/23.1 |

FOREIGN PATENT DOCUMENTS 710542  6/1965  Canada ............................... 73/23.1

Primary Examiner—Stephen A. Kreitman
Attorney, Agent, or Firm—Millen & White

[57] ABSTRACT

An apparatus for feeding carrier gas at a constant rate to on-column injectors for capillary and micropacked gas-chromatographic columns. The apparatus includes a constant pressure gas delivering device in operation during the sample injection, and a constant rate gas delivering device in operation during the sample processing stage inside the column. The two devices are connected in parallel and a switch controls the alternative operation of the same.

4 Claims, 1 Drawing Figure

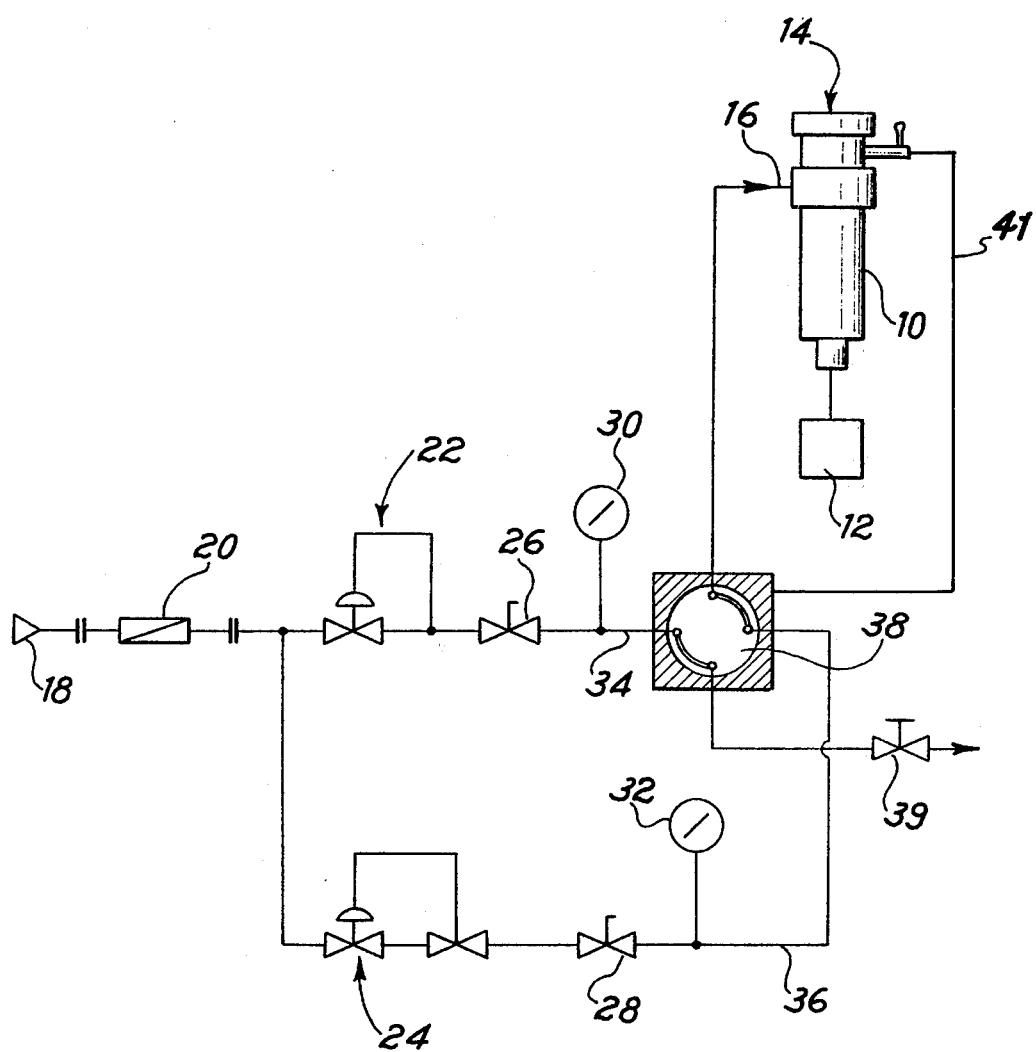

APPARATUS FOR FEEDING CARRIER GAS TO ON-COLUMN INJECTORS

BACKGROUND OF THE INVENTION

1. Field of the Invention

This invention relates to an apparatus for carrying out, at a constant rate, carrier gas feeding of injectors for capillary or micropacked gas-chromatographic columns, more precisely injectors of the so-called on-column type, as for instance described by Grob & Grob (Journal of Chromatography 151, page 311 (1978)).

In particular, this invention relates to a feeding apparatus of the described type, having new and improved features, capable of allowing better and more perfect operative efficiency of the injector-column unit to which this apparatus sends the carrier gas.

2. Description of the Prior Art

As it is known, the above described "on-column" type injectors are used to inject samples into capillary gas-chromatographic columns and are provided with a sealing element which is opened during injection and subsequently closed at the end of injection and during the whole period in which the sample, together with the carrier, constantly flowing into the injector, are introduced into the gas-chromatographic column, which is housed, in turn, in an oven with temperature varying according to a preset program.

Under these conditions, a pressure regulator operating at constant pressure allows maintaining gas constant rate only when operative conditions, and particularly, conditions of temperature and pressure of the system which is fed with gas are constant. This situation occurs, however, only during the sample injection stage, while during the subsequent stage, when a determined program of temperature variation in the column is followed, there are consequently variations in hydraulic resistance of the columns (viscosity variations in the carrier gas). As a result of these variations, the carrier gas rate changes simultaneously with the temperature variation of the column when the type of pneumatic control used keeps the pressure upstream of the column constant. In order to achieve the best possible operative conditions in the column, for the highest precision and reproducibility of results of analyses performed at the column outlet, it is necessary that the carrier gas is fed into the injector in such a way that a constant rate is reached at the column outlet both during the sample injection stage and during the subsequent processing stage in the gas-chromatographic column. Due to the fact that the sealing piece is opened during injection, feeding with carrier gas is not possible during the injection stage, although this kind of feeding may be performed after the injection stage when the carrier gas is exclusively conveyed into the column.

SUMMARY OF THE INVENTION

In order to overcome these difficulties, this invention relates to an apparatus including, between a carrier gas source and a fitting to the injector, a pressure regulating device for introducing gas at constant pressure and a rate regulating device for introducing gas at constant rate, these regulators being positioned in parallel and moreover, a switch being provided to alternatively connect in circuit the pressure regulator, during injection of the sample or samples into column, and the rate regulator during the subsequent processing stage inside the gas-chromatographic column.

As a matter of fact, by introducing the carrier gas through the pressure regulator at constant pressure during the injection stage, a constant rate feeding is practically achieved, as during this stage the operative conditions of the injector-column unit do not change and in particular pressure in this unit does not change. On the contrary, at the end of injection, when, column temperature variation program is followed, carrier gas introduction through the pressure regulator does not allow obtaining the rate constancy that would be desirable for a perfect processing of the substances in the gas-chromatographic column. In this case, switching the feeding on the rate regulator at constant rate allows to obtain said desirable constancy of this rate, which on the contrary, is not achievable during the injection stage due to the injector opening, through which the carrier gas introduced by means of the rate regulator would escape in the atmosphere without entering the column.

Still, according to the invention, on the basis of the temperature and pressure conditions inside the injector-column unit during injection, it is possible to set the pressure regulator at a constant value such as to ensure a carrier gas rate, in this stage, equal to the rate which is obtained in the subsequent stage by setting the rate regulator at a constant value. The switch controlling the alternative feeding through the pressure regulator or through rate regulator is positioned downstream from these regulators, in such a way as not to create discontinuity in feeding due to passage from one regulator to the other; said switch may optionally be automatically actuated, by means of known systems, and associated to the automatic opening and closing of the sealing element in the injector.

BRIEF DESCRIPTION OF THE DRAWINGS

The only FIGURE is a diagrammatic view of the apparatus according to the invention.

DESCRIPTION OF THE PREFERRED EMBODIMENT

With reference to the FIGURE, an "on-column" type injector 10 is connected to a gas-chromatographic column 12, which is in turn positioned in an oven (not illustrated) which controls its temperature conditions.

The "on-column" injector 10, of the specified type, is fed at 14 with the samples to be analysed, through a sealing element (not shown in detail) which is opened during injection and then closed for the subsequent sample processing stage in the column 12. Downstream from the sealing element there is a fitting 16 for introducing a carrier gas, for instance helium, nitrogen, hydrogen or other gas, coming from a suitable source 18 and passing through a filter 20.

Between the filter 20 and the fitting 16 to the injector, the invention proposes the association of two regulating devices, well known in themselves, and particularly a pressure regulating device 22 and a rate regulating device 24, which have been diagrammatically illustrated in the drawing, together with the appropriate closing valves 26 and 28 and with the detecting instruments 30 and 32. The two pressure and rate regulators 22 and 24 are placed on two branches, 34 and 36 respectively, in parallel, and the feeding into fitting 16 is controlled by means of a switch 38 placed downstream the regulators.

As previously stated, the rate regulator 24, which in the FIGURE appears connected in circuit, controls feeding of the injector 10 during the subsequent injection stage, when the conditions in the injector 10-column 12 unit vary due to changes in the column 12 temperature. The rate regulator 24 is consequently set, as described later on, in such a way as to ensure feeding at a constant rate, at a value suitable for the particular analysis to be carried out. During the injection stage, the switch 38 is changed over in order to cut out feeding through the rate regulator 24 and to perform it through the pressure regulator 22, which guarantees feeding in spite of the fact that said sealing element opens on the injector 10. The pressure regulator 22 is set at a constant pressure value, preferably chosen so that, taking into account the operative conditions during injection in the injector 10-column 12 unit, it gives a rate value equivalent to the one set on the rate regulator 24. Therefore, alternatively operating with the pressure regulator 22 and the rate regulator 24, it is possible to obtain a rate of desirable constancy during all the operative stages of said injector 10-column 12 unit. The switch 38 (four-way valve) is suitably positioned downstream from the regulators and functions each time to close the passage to the regulator which is not connected in circuit; this switch may be optionally interlocked, by means of systems and devices known in themselves, as shown by the interlocking means 41 in the FIGURE, to the movement of the sealing element of injector 10, in such a way to be in the position shown in the drawing when the sealing element closes the injector and be in the other position when the sealing element opens the injector for sample injection.

The needle valve 39 is intended to simulate the hydraulic resistance of the chromatographic system at the moment of injection. Its setting is performed only once for determined operative conditions, so that pressure reading on the pressure gauge 32 is equal to that previously established on the pressure gauge 30. In this way, the change over of switch 38 does not involve any pressure variation due to rebalancing of the rate regulator 24.

The closing valves 26 and 28 are used to avoid carrier gas leaks during the inactivity period of the corresponding branch. It must be pointed out that opening of said valves must be performed prior to the injection in a time period sufficient to rebalance the system pressure.

It is obvious that various changes and modifications may be introduced to the described and illustrated configuration without departing from the spirit and scope of the present invention.

We claim:

1. An apparatus for feeding with carrier gas "on-column" type injectors for gas-chromatographic columns, wherein, between the gas source and a fitting to the injector, a pressure regulating device is included to introduce gas at constant pressure and a rate regulating device to introduce gas at constant rate, said regulators being positioned in parallel and moreover a switch being provided to alternatively connect in circuit the pressure regulator during the injection of the sample or samples into the column, and the rate regulator during the subsequent processing stage inside the gas-chromatographic column.

2. An apparatus according to claim 1, wherein said switch is positioned downstream the regulators and closes the outlet of the regulator which is in turn cut out from the circuit.

3. An apparatus according to claim 1, wherein the pressure constant value on which the pressure regulator is set is chosen, in function of the temperature conditions in the injector and column, so as to give, when connected in circuit, a gas rate substantially equal to the rate constant value on which said rate regulator is set.

4. An apparatus according to claim 1, and comprising means for automatically interlocking the switch to the opening and closing of a sealing element of the injector which is opened during injection.

* * * * *